(12) United States Patent
Laeseke et al.

(10) Patent No.: US 11,380,006 B2
(45) Date of Patent: Jul. 5, 2022

(54) SIZE MEASUREMENT USING ANGLE-CONSTRAINED RADIOGRAPHIC IMAGING

(71) Applicant: Wisconsin Alumni Research Foundation, Madison, WI (US)

(72) Inventors: Paul Laeseke, Madison, WI (US); Carson Hoffman, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 358 days.

(21) Appl. No.: 16/749,732

(22) Filed: Jan. 22, 2020

(65) Prior Publication Data

US 2021/0225022 A1    Jul. 22, 2021

(51) Int. Cl.
*G06T 7/60* (2017.01)
*A61B 6/00* (2006.01)
*G06T 7/00* (2017.01)

(52) U.S. Cl.
CPC .............. *G06T 7/60* (2013.01); *A61B 6/4441* (2013.01); *A61B 6/504* (2013.01); *A61B 6/5241* (2013.01); *G06T 7/0014* (2013.01); *G06T 2200/24* (2013.01); *G06T 2207/10116* (2013.01); *G06T 2207/20104* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 5,970,119 A * | 10/1999 | Hofmann | A61B 6/504 378/207 |
| 6,289,235 B1 * | 9/2001 | Webber | G06T 11/008 378/23 |
| 7,885,378 B2 | 2/2011 | Kopans et al. | |
| 2004/0161137 A1 * | 8/2004 | Aben | G06T 7/55 382/128 |
| 2005/0244043 A1 * | 11/2005 | Squilla | G06T 7/0004 382/132 |

* cited by examiner

*Primary Examiner* — Hoon K Song
(74) *Attorney, Agent, or Firm* — Boyle Fredrickson, S.C.

(57) ABSTRACT

A radiography machine provides information about the absolute dimension of imaged objects with as few as two images taken along a common axis at different separations. The information gathered in this way may also be used to deduce absolute or relative separation of the objects along the common axis.

19 Claims, 4 Drawing Sheets

SIZE MEASUREMENT USING ANGLE-CONSTRAINED RADIOGRAPHIC IMAGING

STATEMENT REGARDING FEDERALLY SPONSORED RESEARCH OR DEVELOPMENT

Not Available

CROSS REFERENCE TO RELATED APPLICATION

Not Available

BACKGROUND OF THE INVENTION

The present invention relates to radiographic imaging machines such as x-ray machines and in particular to a radiographic imaging machine providing improved measurement of imaged object dimensions with constrained repositioning of the radiation source.

Radiographic imaging employs high-energy radiation such as kilovoltage x-rays to image the structures within the body that are normally obscured by tissue opaque to visible light. In a common radiographic apparatus, an x-ray source held on a gantry is positioned on one side of a patient who is supported on a table or the like. A detector, such as an array of solid-state radiation sensors, is positioned on the other side of the table to receive radiation transmitted through the patient and attenuated by patient body structure. Each solid-state sensor provides an image pixel recording a brightness value that is a function of transmitted radiation strength at the pixel location.

In its simplest form, a radiographic imaging machine provides only a two-dimensional "shadow" image of the body structure that does not reveal depth or elevation information of the structure along a z-axis normal to the image plane and aligned with the path of the radiation. This lack of depth information can create ambiguity in interpreting the radiographic image, particularly because depth clues such as one structure obscuring another structure are absent because of the translucent representation of tissue in an x-ray image.

It can also be hard to determine the absolute dimension of image structures in a conventional radiograph. This is because of magnification effects caused by diverging rays of radiation from a point radiation source and dependent on an unknown location of the imaged object within the patient. Generally, the size of an object in the image will change according to this unknown distance between the x-ray source and that object and/or the x-ray detector and the object.

When absolute dimensional information must be acquired from a standard radiograph, for example, in order to determine the proper size of a stent or coil for a blood vessel, a fiducial marker may be inserted within the patient near the structure that is to be measured. For example, a catheter with radio-opaque graduations may be threaded into a blood vessel to be close to and within the plane of that blood vessel. Dimensions of the blood vessel can then be scaled directly off of the graduations of this implanted marker used in the manner of a ruler.

Technologies such as computed tomography can provide depth information in imaged objects (as part of a volumetric acquisition) as well as dimensionally accurate images that can be used to determine the absolute size of the imaged structure. The use of such technologies, however, is not always practical in a clinical situation for reasons of cost and equipment availability, as well as the substantial time required to set up such equipment and process the image. The use of a computed tomography machine further may require repositioning of the patient and/or removal of other equipment from the vicinity of the patient, something that can be impractical and, in most cases, increases the time and effort necessary to obtain clinically relevant data. Tomographic imaging techniques relying on multiple exposures over a range of angles can also require an undesirably increased radiation dose.

SUMMARY OF THE INVENTION

The present invention provides a radiographic machine that can provide depth information and accurate dimensions for structures in a patient with as few as two radiographic images taken at a single angle. Limiting the axial motion between images reduces acquisition time and interference between and surrounding medical equipment. The ability to extract depth information about the structure provides important clinical data to the healthcare professional about the location of structures within the body, and dimensionally accurate measurements of body structures allow accurate sizing of stents and the like, without the need for embedded fiducial markers.

Specifically, in one embodiment, the invention provides a radiographic machine having a radiation source and imaging detector held by a support structure on either side of an imaged object along an image axis. An electronic computer communicates with the detector and executes a stored program to (a) receive a first image of the imaged object at a first separation between the radiation source and the imaged object along the image axis and (b) receive a second image of the imaged object at a second separation between the radiation source and the imaged object along the image axis. An electronic computer compares the first and second images and uses data of that comparison to output an absolute size of the imaged object in a dimension perpendicular to the image axis.

It is thus a feature of at least one embodiment of the invention to provide dimensionally accurate information from a limited number of radiographic images without the need for substantial angular repositioning of the radiographic machine such as can be time consuming and can create interference with surrounding equipment or personnel.

The absolute size may be indicated by numeric value.

It is thus a feature of at least one embodiment of the invention to provide a system that can produce quantitatively accurate dimensional measurements in a radiographic image normally subject to arbitrary magnification effects without the need for a reference object.

The electronic computer may further execute the stored program to output an absolute separation along the image axis between the imaged object and at least one of the radiation source and detector in at least one of the first image and second image.

It is thus a feature of at least one embodiment of the invention to provide a simple imaging protocol that can provide depth information along the imaging axis without substantial movement of the radiographic machine. Again, this separation distance may be quantitatively displayed.

In cases where the imaged object includes first and second portions, the electronic computer may output an indication of the relative position of the first and second portions along the image axis.

It is thus a feature of at least one embodiment of the invention to provide important guidance to healthcare practitioners with respect to the relative locations of different objects along the image axis, something that is not always evident from a simple radiograph. This information can be denoted by a variety of different techniques including different shading or coloring in the image or by introducing an occlusion of the first portion by the second portion in the image or vice versa as appropriate.

In one embodiment, the electronic computer may further output an image of the imaged object showing relative position of the first and second portions along an angle differing from the image angle.

It is thus a feature of at least one embodiment of the invention to permit development of a pseudo-3D image from information taken along a single axis.

The radiographic imaging machine may include an object positioner such as a patient table communicating with the electronic computer, and the support structure may provide information to the electronic computer describing an angle of the image axis. The electronic computer may then communicate with the object positioner to move the object positioner according to the angle of the image axis between acquisition of the first image and second image.

It is thus a feature of at least one embodiment of the invention to allow coordination of a patient table and radiographic imaging machine to perform the protocol of the present invention, in either a dedicated machine/table system or when using a portable x-ray machine moving among different tables.

The electronic computer may output the absolute size of the imaged object by measuring a change in dimension of the imaged object between the first and second images and applying this to a function of separation change, the latter being a difference between the first separation and second separation.

It is thus a feature of at least one embodiment of the invention to deduce absolute position from a change in apparent size of an image, something that can be measured with axial relocation of the x-ray source.

The electronic computer may further compute an error value in the absolute size of the image object and display the error value based on resolution of the image detector and length.

It is thus a feature of at least one embodiment of the invention to provide quantitative measurements on radiographic images without suggesting unavailable precision.

In cases where the imaged object includes stationary tissue and the probe is movable through the tissue, the electronic computer may further execute the stored program to determine an absolute separation along the image axis between the probe and at least one of the radiation source and detector and an image size of the probe in at least one of the first and second images. The computer may then determine changes in the absolute separation of the probe according to changes in a size of images of the movable probe in subsequent images.

It is thus a feature of at least one embodiment of the invention to allow tracking axial elevation of a probe such as a catheter in each of a series of images without the need for movement of the x-ray source between acquisitions of the series of images.

The electronic computer may further execute the stored program to output a display of an image of the imaged object from radiation passing through the imaged object from the radiation source to the detector and to receive input from user inputs describing a desired region of measurement through the manipulation of graphic elements on the image.

It is thus a feature of at least one embodiment of the invention to allow the user to specify a region of interest for measurement to optimize positioning of the imaged object and/or to provide for graphic tools indicating the desired dimensional measurements.

The electronic computer may determine a magnification map between the first and second images by piecewise matching of regions of the first and second images at different magnifications, and wherein the magnification map is used to determine absolute size of the imaged object.

It is thus a feature of at least one embodiment of the invention to overcome the difficulties of manually identifying dimensions in images through the use of an areal matching process.

These particular objects and advantages may apply to only some embodiments falling within the claims and thus do not define the scope of the invention.

DETAILED DESCRIPTION OF THE PREFERRED EMBODIMENT

Figure 1:
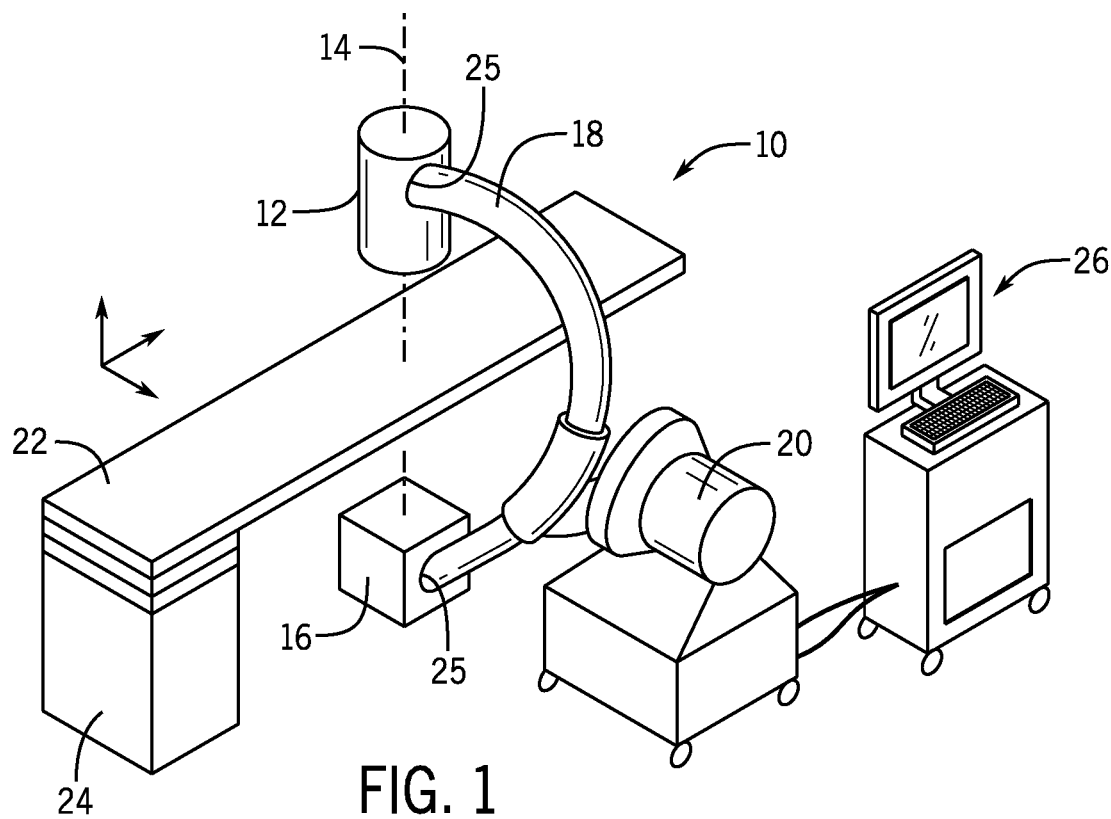
FIG. 1 is a simplified perspective view of a radiography machine having a radiation source and imaging detector that may be positioned on either side of patient (not shown) when the patient is supported on a table.

Referring now to FIG. 1, a radiographic imaging machine 10 may have a radiation detector 12 positioned to receive radiation along an axis 14 from a radiation source 16 positioned to project radiation also along axis 14. The radiation detector 12, for example, may be a standard radiographic image sensor, for example, providing for a rectilinear array of rows and columns of solid-state detectors that can detect and produce an image at a variety of pixel locations in the manner of a camera. The radiation source 16, for example, may be an x-ray tube or other radiation source producing kilovoltage or megavoltage radiation.

The radiation detector 12 and radiation source 16 may be positioned and supported together on a gantry arm 18, for example, on opposite ends of a C-arm. The gantry arm 18 may be flexibly repositioned by a base unit 20 to allow the axis 14 to be changed in angle through a range of azimuthal and altitudinal angles in three dimensions with respect to and projecting through a table 22.

The table 22 may have a generally radiolucent horizontal supporting surface for supporting and positioning a patient (not shown) for imaging and may in turn be supported above the floor by a motorized pedestal 24. The motorized pedestal 24 operates to allow the table 22 to be raised and lowered in elevation as well as shifted right or left and longitudinally forward or backward along its longest axis, all under computer control. Operating together, the base unit 20 and pedestal 24 permit the radiation detector 12 and radiation source 16 to be positioned so that the axis 14 can intersect an arbitrary location within the patient's body at an arbitrary angle.

In addition, the base unit 20 and pedestal 24 operating individually or together allow movement of either or both of the radiation detector 12 and radiation source 16 together and apart along axis 14. In addition or alternatively, the radiation detector 12 and radiation source 16 may be supported on motorized slides 25 with respect to the gantry arm 18 to provide such motion with respect to the gantry arm along the axis 14.

The base unit 20 and various elements attached to the gantry arm 18 may communicate with a control console 26 allowing for a healthcare professional to control the radiographic imaging machine 10 as well as receive radiographic image information as will be discussed below.

Figure 2:
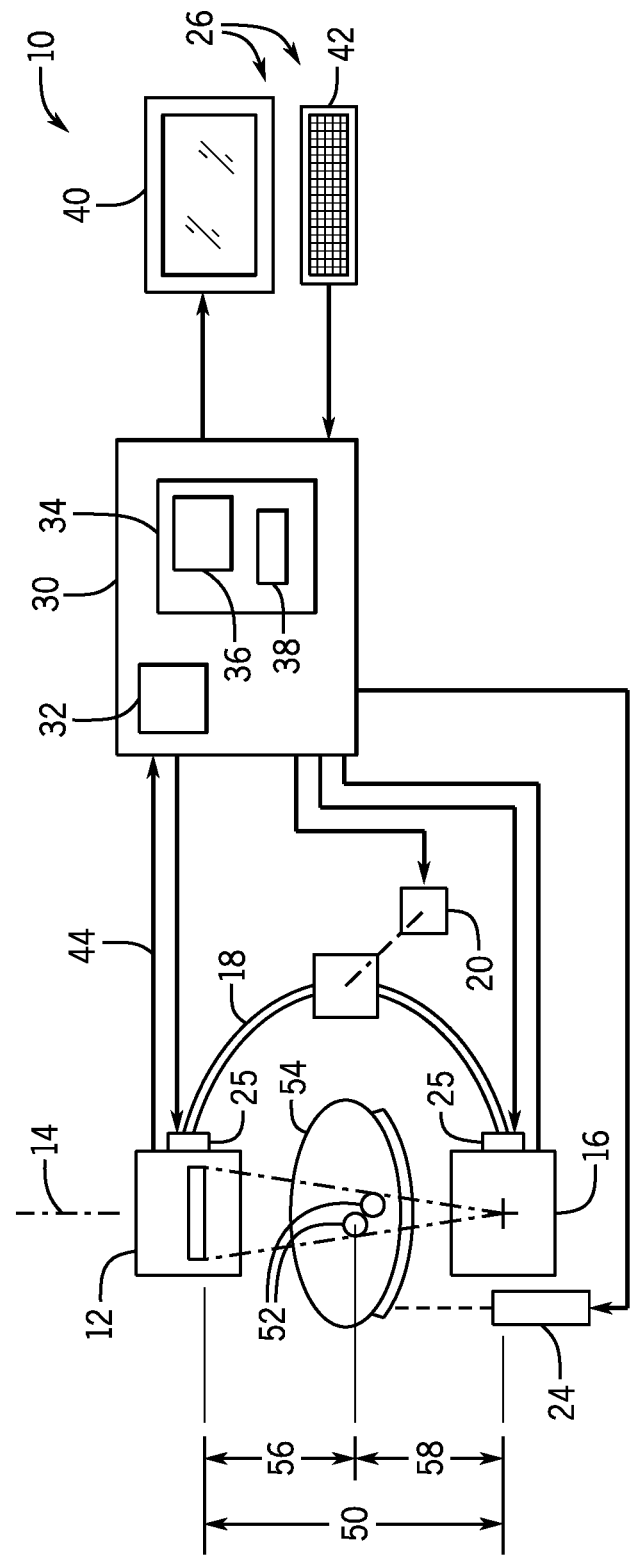
FIG. 2 is a block diagram of the radiography machine of FIG. 1 showing an electronic computer controlling the various components of the radiography machine and in communication with a display terminal.

Referring now also to FIG. 2, the console 26 may provide an electronic computer 30 having one or more processors 32 communicating with computer memory 34, the latter of which may hold a program 36, to be described in further detail below, as well as various data files 38 including image information and the like. The computer 30 may communicate with a terminal providing a display screen 40 and a user input device 42 for outputting and receiving information, respectively, to and from a healthcare professional as will be discussed. During operation, the computer 30 will receive image information 44 from the radiation detector 12, for example, providing a set of x-ray intensity values at different coordinate locations over a two-dimensional plane, to reconstruct and display a two-dimensional radiographic image. Generally the computer 30 may also provide control signals to turn on and off the radiation source 16 and the control the motors of the base unit 20, pedestal 24, and slides 25 to control the angulation and positioning of the radiation source 16 and radiation detector 12 as discussed above. This control may be conducted open loop or by means of feedback loops with appropriate sensors on the individual axes' motors.

Figure 3:
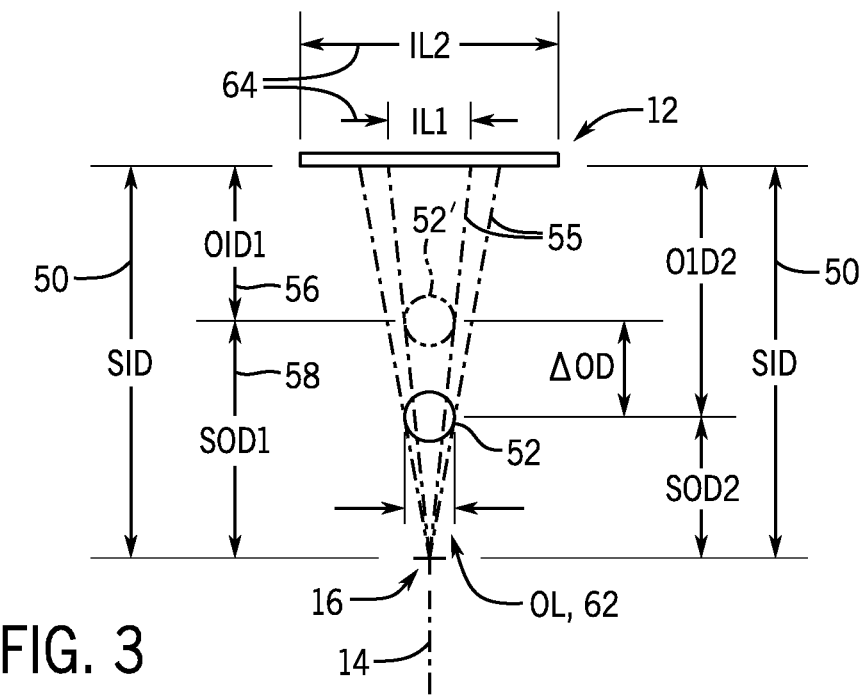
FIG. 3 is a geometric representation of the diverging radiation from the radiation source such creates a magnification of structure displayed in an image acquired by the imaging radiation detector showing various dimensions relevant for an example operation of the present invention.

Referring now also to FIG. 3, during control of the radiographic imaging machine 10, the computer 30 may receive configuration information either from a user or electronic sensors attached to the gantry arm 18 defining a source-to-image detector distance (SID) distance 50. In addition, the computer 30 may move the radiation source 16 and radiation detector 12 to change an object-to-image detector distance (OID) 56 between one or more image objects 52 in a patient 54 and a plane of the imaging detector 12. This movement may also be used to independently or correspondingly change a source-to-object distance (SOD) 58 between one or more imaged objects 52 and an origin point of the radiation source 16 from which radiation rays 55 emanate.

As best seen in FIG. 3, the generally diverging pattern of radiation rays 55 from the radiation source 16 will generally produce a magnification of absolute dimensions of an imaged object 52 within an image plane generally parallel to the surface of the image detector 12. Thus, for example, an object length (OL) 62 of an imaged object 52 will differ in scale from the corresponding image length (IL) 64 discernible from an image produced by the radiation detector 12.

As noted above, the program 36 executed by the computer 30 may operate to provide absolute dimensional measurements (e.g., OL) of an imaged object 52 as well as absolute or relative elevational measurements (SOD or OID) of an imaged object 52 with as few as two images taken along a single axis 14 with respect to the patient 15. This ability greatly reduces interference with clinical procedures and the time required to obtain important dimensional or elevational information.

Figure 4:
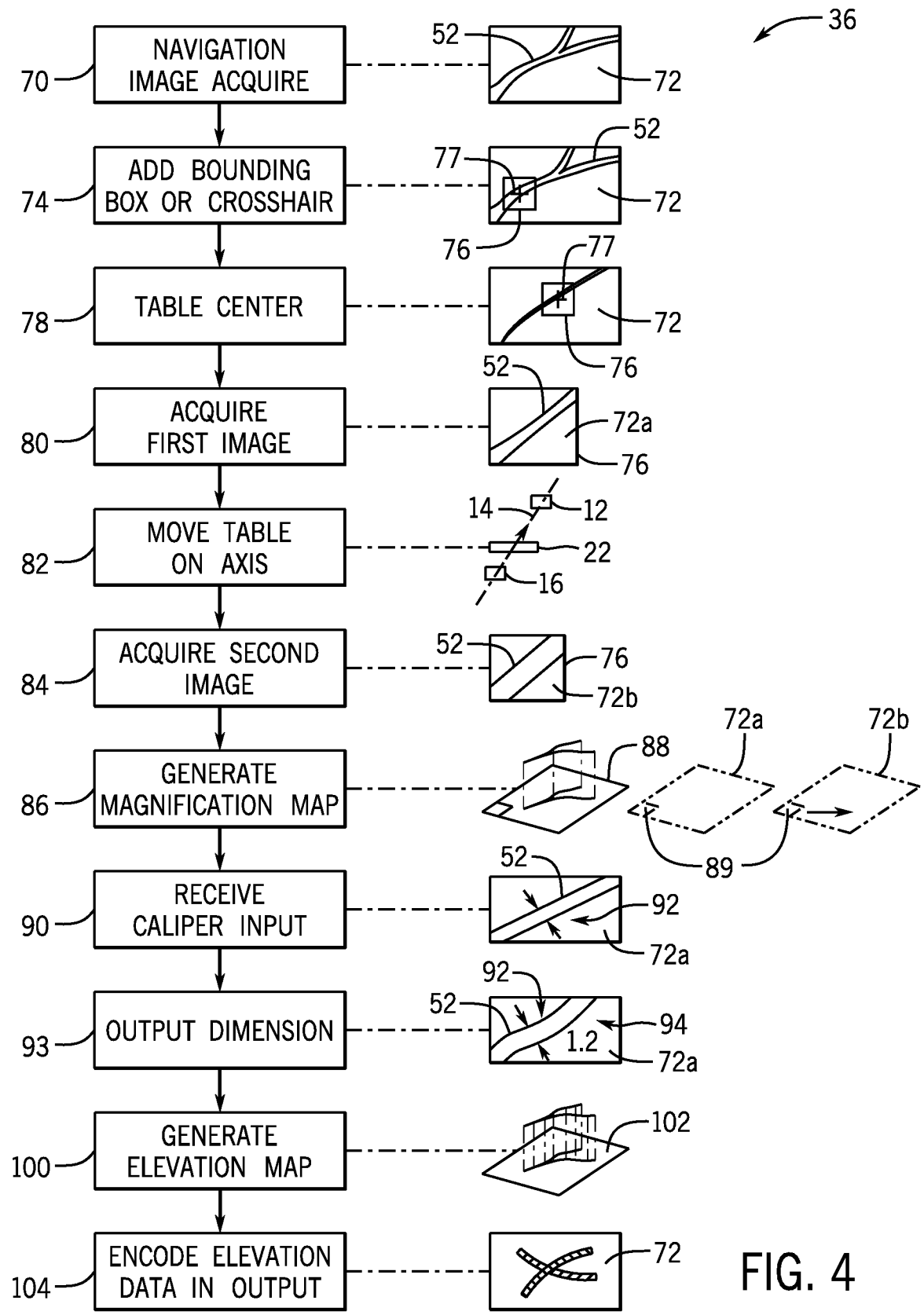
FIG. 4 is a flowchart with pictorial representations of the various steps of a program executable by the computer of FIG. 2 for implementing one embodiment of the invention.

Referring now also to FIG. 4, at a first step of the program 36 executed by the computer 30, indicated by process block 70, the radiation source 16 and radiation detector 12 are positioned about the patient 54 to provide a clinically desired two-dimensional planar image 72 of the imaged object 52. This image 72 may be displayed on the display 40 and provides clinical information in its own right as well as a framework for navigation and a background for describing dimensional measurements of imaged objects 52 desired by the healthcare professional. Positioning of the radiographic imaging machine 10 may be, for example, through commands on the console 26 provided by the healthcare professional or manually as is well understood in the art.

At subsequent process block 74, the healthcare professional working on the console 26 may place a bounding box 76 or a crosshair 77 on the image 72, surrounding or centered on a region where additional information is required, for example, where an absolute dimension of the imaged object 52 or its relative or absolute elevation with respect to other imaged objects 52 is desired. This bounding box 76 may be located by the physician using a cursor control device according to techniques well known in the art.

At optional process block 78, after the bounding box 76 is located, the pedestal 24 may be activated by the computer 30 to center the bounding box 76 within the image 72. This centering is such as to minimize the aggregate angle of the radiation rays 55 passing through the imaged object 52 with respect to a surface normal of the plane of the radiation detector 12 thereby improving the accuracy of the measurements of elevation and dimension. Generally, this centering reduces a second-order effect in magnification caused by divergence of the radiation from the radiation source 16 such as provides nonuniform magnification at the edges of the image 72. Nevertheless, the invention alternatively contemplates that such an offset may be accommodated by mathematical compensation using basic geometric principles.

At succeeding process block 80, a first image 72a is acquired of the imaged object 52 within the bounding box 76, or a portion of navigation image 72 may be used at this step. In either case, this first image 72a will be obtained with a first relative positioning between the imaged object 52 and radiation source 16, as shown in FIG. 2, defined by first value SOD1 describing a "source-object distance" between the radiation source 16 and the imaged object 52 or a second value OID1 describing an "object-image distance" between the imaged object 52 and the radiation detector 12 related to the first value by a known distance between the source and detector. These values OILD1 and SOD1 are generally unknown by the computer 30 or the healthcare professional and cannot be directly measured because they relate to material at an unknown location inside the patient 54.

At process block 82, the computer 30 controls the pedestal 24 and/or base unit 20 to move the table 22 (and thus the patient 54) along the axis 14 with respect to the radiation source 16 and radiation detector 12. This motion is ideally done without changing the relative angle of the axis 14 with respect to the table 22 or patient 54. After this movement, the object 52 is positioned relative to the radiation source 16 and radiation detector 12 as shown by phantom object 52' in FIG. 3.

Ideally this motion does not change the distance between the radiation source 16 and radiation detector termed SID but nevertheless provides new separation values between the imaged object 52 and the radiation source 16 and 20 imaged object 52 and the imaging detector 12 of OID2 and SOD2. The value of SID will also be generally known by the computer 30 either input by the user or by sensors on the radiographic imaging machine 10. Holding the value of SID constant simplifies calculations and the mechanism of the radiographic imaging machine 10.

While the values of OILD1, SOD1, OILD2, and SOD2 are unknown, the value of ΔOD, being the difference between the values of OILD1 and SOD1 and also the difference between the values of OILD2 and SOD2 may be readily determined by sensors on the radiographic imaging machine 10 or by the computer 30 monitoring its movement commands to the radiographic imaging machine 10. This movement of process block 82 can be performed automatically by the computer 30 through communication between the base unit 20, pedestal 24, and the computer 30. Such coordination can be implemented through the standard communication pathways of an integrated radiographic imaging machine 10 or can be implemented by means of wireless intercommunication between an arbitrary motorized table 22 and a mobile C-arm system movable among multiple different tables 22.

It should be noted that this movement is relative and can be implemented either by movement of the table 22 or, with the table 22 fixed, with movement of the gantry arm 18, or with the table 22 and the gantry arm 18 fixed and movement of the radiation detector 12 and radiation source 16 on slides 25 with respect to the gantry arm 18 or by combinations of the above.

As indicated by process block 84 of FIG. 3, after completion of this movement of process block 82, a second image 72b may be acquired capturing data within the bounding box 76. In this respect, the bounding box 76 may be mapped to a larger size in image 72b to ensure all of the data within the bounding box 76 of image 72a is also captured in image 72b.

Referring now to process block 86, the first image 72a and second image 72b may be compared to generate a magnification map 88 indicating a general change in the dimensions of the imaged objects 52 within the images and thus changes in effective magnification of the imaged objects 52 such as reveal information about their dimension and placement. This magnification map 88 provides an array of value corresponding to the array of pixels of the images 72 but mapped to magnification values at those pixels rather than radiation intensity. In one embodiment, the magnification map 88 may be obtained, for example, by examining correspond small regions 89 of each of the images 72 around each pixel and applying various degrees of magnification to the region of one of the images 72a to find a best match with the corresponding region in image 72b, for example, by looking at correlation or mutual information or the like. The magnification at the best match indicates the magnification at that pixel.

The known movement of the imaging machine 10 per process block 82 and knowledge of the SID 50 can be used to provide a limited range through which the matching process should be conducted, speeding up this process and ensuring that the magnification values are within reasonable limits.

After each pixel is examined, this process is repeated at a next pixel successively over the images to provide a piecewise comparison over the entirety of both images 72. This matching process may be augmented by considering minor translations of the images with respect to each other and rotations of the images with respect to each other. Ideally, the magnification map 88 may be limited to the imaged object 52, for example, using automatic segmentation techniques or the like based on an identification of that imaged object 52 automatically or by a user.

This magnification map 88 may be displayed directly, for example, with the magnification values superimposed as color on the otherwise monochromatic pixel values of one or more of the images 72 to provide a very rough indication of the relative elevation of each portion of the image. Those portions exhibiting greater magnification being closer to the radiation source 16 can have a corresponding different color. The invention contemplates, that this magnification map 88, however, is not used directly but instead is used later in a quantitative calculation to be described.

Referring now to process block 90 of FIG. 4, the user may optionally next enter commands to the console 26 to identify a dimension to be measured. In one example, a "caliper" widget 92 may be applied to the image 72a under user control to define a desired dimension of an imaged object 52 be measured in that image. In this example, the caliper widget 92 may provide for two pointers having controllable variable separation that may be manually located at opposite endpoints of the desired measurement along the desired measurement axis. This separation may be augmented with a "snap-to" feature to help identify these endpoints, for example, by interrogating the underlying image data to find a high contrast indicating a boundary of an imaged structure such as a blood vessel. It will be appreciated that other techniques for automatically locating the precise location of the measurement may be employed including those that average data within a region or try to fit the data to a model of the measured structure (e.g., a blood vessel), the model having defined endpoints for linear measurements. The separation between the caliper pointers in this example provides a first image dimension IL1 shown in FIG. 3.

A second image dimension ILD2 72b is then obtained by the healthcare professional setting a second caliper widget 92 at the same location on the second image 72b with or without the snap-to assistance. Alternatively, this dimension may be automatically acquired by generating the measurement endpoints in image 72b by mapping the endpoints of the measurement in image 72a to image 72b using the magnification map 88.

After values of SID, ΔOD, ILD1, and ILD2 have been acquired, they may be used to compute the value of SOD1 through the formula:

$$SOD1 = \Delta OD/(1-(IL1/IL2)) \quad (1)$$

Once the value of SOD1 has been determined, OID1 may be computed from the known value of SID, and using the value of ΔOD, the values of SOD2 and OID2 may likewise be readily computed with simple steps of addition or subtraction as will be apparent to those of ordinary skill in the art from the diagram of FIG. 3. These values alone or together establish the relative location in elevation of the object 52 and, when multiple objects 52 are imaged, can show the relative or absolute separation in elevation along axis 14 between those multiple objects 52.

Next, the desired dimension OL of the imaged object 52 may be obtained by the formula:

$$OL = IL1 * (SOD1/SID1) \quad (2)$$

$$\text{or } OL = IL2 * (SOD2 * SID2) \quad (3)$$

Note that this determination of absolute dimension does not require a priori knowledge of the absolute elevation of the imaged object 52 with respect to either the radiation detector 12 or radiation source 16 before the calculation of equation (1) above and avoids the need for any absolute size reference marker such as a fiducial marker visible in the images 72.

While only two images 72a and 72b are described, it will be appreciated that this process can be iteratively perform with multiple images 72, for example, taken at various points along the movement of the radiographic machine radiation detector 12 and radiation source 16 along axis 14 per process block 82 to provide for even higher levels of accuracy.

This above approach does not require the magnification map 88 collected at process block 86 because separate measurements of IL1 and IL2 are made. In an alternative approach a single measurement (e.g. IL1) may be made using, for example, a caliper widget, and the magnification map 88 may be used to obtain values of IL1/IL2 to compute SOD1 per equation (1) above. The value of OL can then be obtained without additional measurement using equation (2). It will be appreciated that a similar result can be obtained by making a single measurement of IL2 and using the magnification map 88.

Referring now to process block 93, the desired output dimension 94 may be displayed on the image 72a near the widget 92 in numeric form. It will be appreciated that other methods of output or display of the desired output dimension OL may be used including, for example, providing a ruler superimposed on the image 72 that has been adjusted in length according to the calculations provided above. Specific measurements can be automated, for example, to allow user to click on a vessel and have the diameter appear.

Referring now to process block 100, as noted, any of the values of SOD1, OID1, SOD2, and OID2 can be used to provide useful information about the elevation of the imaged object 52 within the patient 54 in a direction perpendicular to the image plane and in particular to relative locations of two imaged objects 52 with respect to each other in non-overlapping portions of the images 72a and 72b. The result of this calculation done at multiple points over the images 72 may produce an elevational map 102 similar to the magnification map 88 but associating each pixel with an elevational value. Desirably, the elevational map may also be applied only to the imaged object 52 to eliminate artifacts caused by background tissue.

Figure 5:
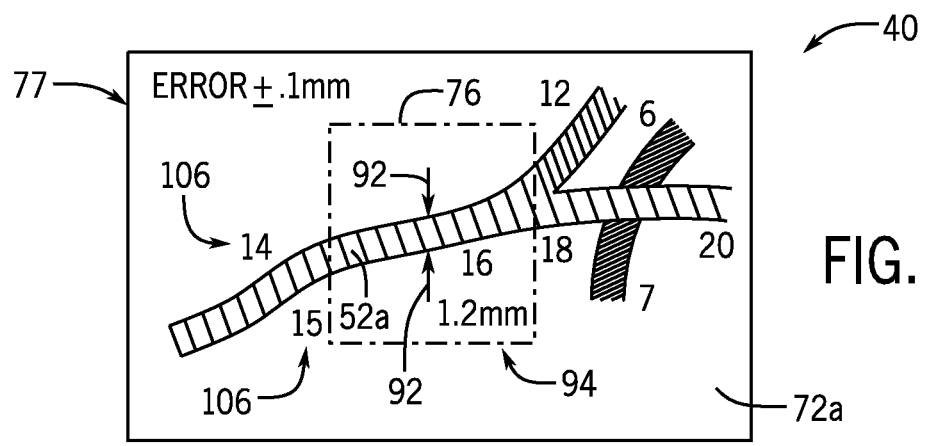
FIG. 5 is a screen display that may be produced on the display terminal of FIG. 2 showing a display of absolute dimension and relative and absolute elevation of portions of an imaged object.

Using the elevational map 102, for example, the higher and lower of imaged blood vessels can be resolved as well as the separation distance between these blood vessels along the axis 14. More generally, per process block 104, this elevational information may be encoded into an output image 72 to provide additional clinical information to the physician. Referring now also to FIG. 5, in one embodiment elevational information may be encoded, for example, in a varying color of the imaged object here shown by cross-hatching of varying pitch. Depth or elevational markers 106 may also be placed close to the image object to provide elevational information. When there are multiple imaged objects 52a and 52b in the image 72, this elevational information may be used to elide image information on one of the imaged objects 52b when it overlaps the other imaged object 52a to provide a sense of visual occlusion that intuitively denotes a foreground and background object. The elevation of tissue in the actual region of overlap can be ambiguous in the present invention but can be determined by extrapolation of data on either side of the overlap.

The computer 30 may also operate to provide an error value 77 qualifying the output dimension 94 and/or elevational information. This error value 77 may be deduced, for example, from the known spatial resolution of the radiation detector 12 and the relative size of quantitatively displayed measurements by computing the quantization error in such measurements caused by the discrete boundaries of the pixels of the image detector in light of the known magnification. More sophisticated methods for the determination of error value 77 may be provided, for example, evaluating the quality of matching or correlation performed during generation of the magnification map 88, offset of the location of the measurement value from the the center of the image 72, and the like. It will be appreciated that this error value 77 may be alternatively expressed, for example, by truncating the precision of the output dimension 94 or the like.

Figure 6:
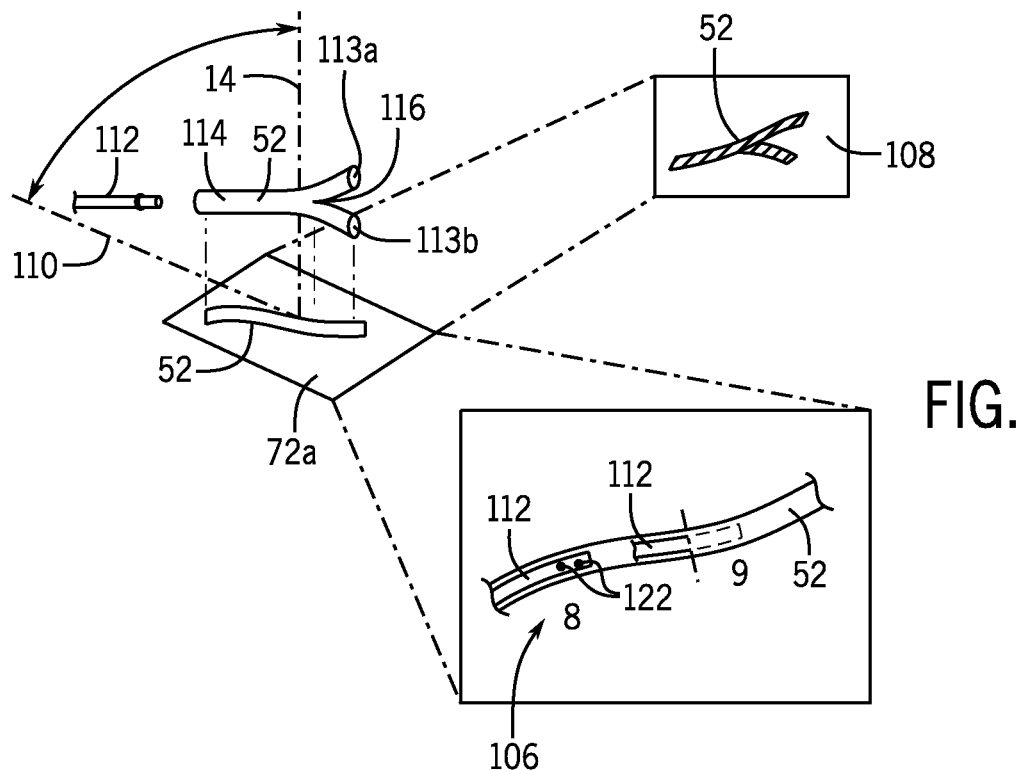
FIG. 6 is a representation of an imaged blood vessel receiving a catheter and showing a pseudo-three-dimensional representation of that blood vessel possible with the present invention and a system for tracking the catheter as it passes through the blood vessel.

Referring now to FIG. 6, it will be appreciated that this elevational information may be used to create a pseudo-3D image 108 showing the imaged objects 52 as if viewed from an angle along an axis 110 canted with respect to axis 14. This image 108 is pseudo-three-dimensional because depth thickness information on the imaged object 52 is not known and, accordingly, these elements are shown as flat strips of no axial dimension. Nevertheless, this image 108 may provide for useful information about relative elevational positions of different imaged structures. When imaged object 52 can be classified, this flat depth information may be augmented, for example, with pre-existing models of blood vessels or procedural models which indicate the blood vessels are substantially round in cross-section.

Referring still to FIG. 6, the present invention can be usefully applied to procedures in which instruments inserted within the body need to be tracked with respect to other tissue. For example, the invention may be used with a catheter 112 that is being threaded within a blood vessel 114. In this situation, near real-time tracking of the tip of the catheter 112 may be desired particularly when the catheter reaches a point of bifurcation 116 in the blood vessel 114. Particularly when that bifurcation is in the vertical plane, it can be difficult to determine from a conventional radiograph whether the catheter 112 has passed into the upper branch 113a or the lower branch 113b.

Figure 7:
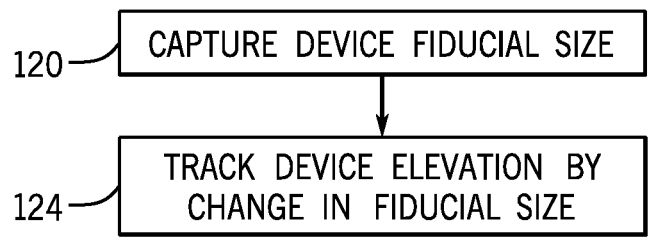
FIG. 7 is a flowchart showing additional steps used for the process of FIG. 3 with respect to tracking the catheter or similar device.

To address this situation, the present invention may include program steps including program step 120 shown in FIG. 7 in which a dimensional aspect of the catheter 112, for example, fiducial markers 122 on a tip of the catheter 112, are measured in one of the images (e.g., image 72a) and this dimension associated with a particular elevation of the blood vessel (or catheter tip) at that location using the two-image process described above.

Then as indicated by process block 124, without obtaining additional pairs of images necessary for process blocks 80 and 84, the relative height or elevation of the tip of the catheter 112 (denoted SODnew) may be determined by tracking a change in the size of the fiducial object 122 as it moves through successive images 72 according to the formula $$SODnew = SOD0(IFL/IFL') \quad (3)$$

where:

IFL is the fiducial dimension in the original image linked to a particular SOD value (SOD0) and IFL' is any subsequent fiducial dimension measured in the subsequent image with no movement of the radiographic imaging machine 10.

Knowledge about the height of the imaged object 52 deduced per equation (3) and knowledge about the elevation of the blood vessel 114 at various locations may be used to determine whether the catheter 112 has passed into the upper branch 113a or lower branch 113b. The passage of the catheter 112 into the lower branch 113b may be depicted as shown by modifying the image of the catheter in the lower branch, for example, to elide its image out or change its color. This information may also be used, for example, to confirm a location against a prior acquired 3D volume and may be used, for example, to provide a cursor or other marker positioned with respect to that 3D volume.

While the invention has described various methods of expressing the information about relative elevation in terms of color, shading, or overlap, it will also be appreciated that this data may be used to form a stereoscopic image with the structure shifted slightly left or right for different eyes of a human observer to produce a sense of depth. Further, the present invention describes acquiring as few as two images along a single axis, and it will be appreciated that this technique may be augmented with additional images along that axis and further that slight angular variations between the images, for example, plus or minus five degrees, may be accommodated for symmetrical objects using the principles of the present invention.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

APPENDIX

Derivation of Formulas with Reference to FIG. 3

Variable Definitions

Source to Image Distance=SID; Source to Object Distance=SOD; Object to Image Distance=OID, Magnification=MAG; Image Length=IL (measured from image); Object Length=OL, Displacement of Object=$\Delta$OD Relationship Definitions MAG=IL/OL;
MAG=SID/SOD;
SID1=SID2
$\Delta$OD=OID1−OID2;
OID2=OID1−$\Delta$OD
$\Delta$OD=SOD2−SOD1
SOD2=SOD1+$\Delta$OD
Derivation
MAG1/MAG2=((SID1/SOD1))/((SID2/SOD2))=SOD2/SOD1 (divide Mag keep SID constant)
MAG1/MAG2=((IL1/OL1))/((IL2/OL2))=IL/IL2 (Calculate Mag Ratio From Images)
IL1/IL2=SOD2/SOD1=(SOD1−$\Delta$OD)/SOD1=1−$\Delta$OD/SOD1 (Substitute mag ratio and simplify)
IL1/IL2−1=−$\Delta$OD/SOD1 (Reorganize to get SOD1 on one side)
1−IL1/IL2=$\Delta$OD/SOD1 (Reorganize to get SOD1 on one side)
SOD1=$\Delta$OD/(1−IL1/IL2); or SOD1=($\Delta$OD (IL2/IL1))/((IL2/IL1)−1)
(Organized for Both IL Ratios)
Once SOD is calculated for one image it is used to compute OL1, OL2, MAG1, MAG2, SOD2, and the ratio IL1*SOD1=IL2*SOD2 is used to calculate new SOD's at any height.

What we claim is:

1. A radiographic machine comprising:
a radiographic radiation source;
an imaging radiation detector;
a support structure adapted to hold the radiographic radiation source in opposition to the imaging radiation detector about an imaged object along an image axis positioned with respect to the imaged object; and
an electronic computer communicating with the imaging radiation detector and executing a stored program to:
(a) receive a first image of the imaged object from radiation passing through the imaged object from the radiographic radiation source to the imaging radiation detector at a first separation between the radiographic radiation source and the imaged object along the image axis;
(b) receive a second image of the imaged object from radiation passing through the imaged object from the radiographic radiation source to the imaging radiation detector at a second separation between the radiographic radiation source and the imaged object along the image axis; and
(c) output an absolute size of the imaged object in a dimension perpendicular to the image axis from a comparison of the first image and second image.

2. The radiographic machine of claim 1 wherein the absolute size is indicated by a numeric value.

3. The radiographic machine of claim 1 wherein the electronic computer further executes the stored program (d) to output an absolute separation along the image axis between the imaged object and at least one of the radiographic radiation source and imaging radiation detector in at least one of the first image and second images.

4. The radiographic machine of claim 1 wherein the absolute separation is indicated by a numeric value.

5. The radiographic machine of claim 1 wherein the imaged object includes first and second portions and wherein the electronic computer further executes the stored program (d) to output an indication of relative position of the first and second portions along the image axis.

6. The radiographic machine of claim 5 wherein the electronic computer further outputs an image of the imaged object and wherein the relative position of the first and second portions is indicated by at least one of a different shading in the image between the first and second portions, a different coloring in the image between the first and second portions, and an occlusion of the first portion by the second portion in the image.

7. The radiographic machine of claim 1 wherein the electronic computer further outputs an image of the imaged object showing the relative position of the first and second portions along an angle differing from the image angle.

8. The radiographic machine of claim 1 wherein the imaged object includes first and second portions and wherein the electronic computer executes the stored program to (d) output a first absolute size of the first portion and a second independent absolute size of the second portion.

9. The radiographic machine of claim 1 further including an object positioner communicating with the electronic computer and holding the imaged object and wherein the support structure provides information to the electronic computer describing an angle of the image axis and wherein the electronic computer communicates with the object positioner to move the object positioner according to the angle of the image axis between acquisition of the first image and second images.

10. The radiographic machine of claim 1 wherein the electronic computer outputs the absolute size of the imaged object by measuring a change in dimension of the imaged object between the first and second images and a separation change, being a difference between the first separation and second separation.

11. The radiographic machine of claim 10 wherein the change in dimension of the imaged object is IL1/IL2 and the separation change is a distance $\Delta OD$ and the absolute size OL is determined according to a formula:

$$OL = IL(((\Delta OD/(1-IL1/IL2))/SID))$$

where:
IL is the apparent size of the imaged object at the imaging radiation detector and
SID is a distance of separation between the imaging radiation detector and the radiographic radiation source.

12. The radiographic machine of claim 1 wherein the electronic computer controls the support structure to provide a predetermined separation change.

13. The radiographic machine of claim 1 wherein electronic computer further computes an error value in the absolute size of the imaged object and displays the error value based on resolution of the image detector and length.

14. The radiographic machine of claim 1 wherein the imaged object includes stationary tissue and a probe movable through the tissue and wherein the electronic computer further executes the stored program to (d) determine an absolute separation along the image axis between the probe and at least one of the radiographic radiation source and imaging radiation detector and an image size of the probe in at least one of the first and second images and to (e) determine changes in the absolute separation of the probe according to changes in an image size of the probe in a series of subsequent images of the imaged object from radiation passing through the imaged object from the radiographic radiation source to the imaging radiation detector.

15. The radiographic machine of claim 1 wherein electronic computer further executes stored program to output a display of an image of the imaged object from radiation passing through the imaged object from the radiographic radiation source to the imaging radiation detector and to receive input from a user describing a desired region of measurement through a manipulation of graphic elements on the image.

16. The radiographic machine of claim 15 wherein the graphic elements indicate at least one of a region of interest of the measurement and a dimension line along which measurements should be taken.

17. The radiographic machine of claim 1 wherein the electronic computer determines a magnification map between the first and second images by piecewise matching of regions of the first and second images at different magnifications and wherein the magnification map is used to determine absolute size of the imaged object.

18. The radiographic machine of claim 1 wherein a separation between the radiographic radiation source and imaging radiation detector is held fixed between acquisition of the first image and second images.

19. The radiographic machine of claim 1 wherein the electronic computer compares the first image and second images to produce the absolute size independent of information about a distance between the imaged object and the radiographic radiation source or imaging radiation detector and independent of information about a size of a reference object of known dimension in the first or second images.

* * * * *